(12) United States Patent
Kumamoto et al.

(10) Patent No.: US 8,084,139 B2
(45) Date of Patent: Dec. 27, 2011

(54) ARTICLE FORMED INTO SHEET, METHOD FOR PRODUCING THE SAME AND EXOTHERMIC FORMED ARTICLE

(75) Inventors: Yoshiaki Kumamoto, Tochigi (JP); Masataka Ishikawa, Tochigi (JP)

(73) Assignee: Kao Corporation, Tokyo (JP)

( * ) Notice: Subject to any disclaimer, the term of this patent is extended or adjusted under 35 U.S.C. 154(b) by 1302 days.

(21) Appl. No.: 11/579,595

(22) PCT Filed: Apr. 28, 2005

(86) PCT No.: PCT/JP2005/008243
§ 371 (c)(1),
(2), (4) Date: Jan. 22, 2007

(87) PCT Pub. No.: WO2005/108674
PCT Pub. Date: Nov. 17, 2005

(65) Prior Publication Data
US 2008/0292879 A1 Nov. 27, 2008

(30) Foreign Application Priority Data

May 7, 2004 (JP) ................................ 2004-139199
Jun. 7, 2004 (JP) ................................ 2004-168010

(51) Int. Cl.
*B32B 29/00* (2006.01)
(52) U.S. Cl. .................. 428/537.5; 442/292.1; 162/218
(58) Field of Classification Search ............... 428/537.5; 162/218; 442/292.1
See application file for complete search history.

(56) References Cited

U.S. PATENT DOCUMENTS 6,830,658 B2 * 12/2004 Kumamoto et al. .......... 162/219
7,749,357 B2 * 7/2010 Kumamoto et al. .......... 162/218

FOREIGN PATENT DOCUMENTS

| JP | 1-132897 | 5/1989 |
|---|---|---|
| JP | 1-201253 | 8/1989 |
| JP | 7 229097 | 8/1995 |
| JP | 2572621 | 10/1996 |
| JP | 2000-303399 | 10/2000 |
| JP | 2002 176286 | 6/2002 |
| JP | 2003 55888 | 2/2003 |
| JP | 2003-89994 | 3/2003 |
| JP | 2003 102761 | 4/2003 |
| JP | 2004-16010 | 1/2004 |
| WO | 2004 041135 | 5/2004 |

OTHER PUBLICATIONS

Teruo Watanabe, "Operation Experiences Adapted the Polyionic Complex System to PM's Wet End to Stabilize Retention", Japan Pulp Paper, vol. 52, No. 12, Dec. 1998, pp. 1717-1725 (with English abstract and partial English translation).
U.S. Appl. No. 12/063,476, filed Feb. 11, 2008, Ishikawa, et al.
European Search Report mailed Mar. 2, 2011, in European Patent Application No./Patent No. 05736961.3—2124/1770212 PCT/JP2005008243.
Notice of Rejection issued Jan. 18, 2011, in Japanese Patent Application No. 2004-131398 (with English translation).
European Office Action issued Sep. 1, 2011, in European Patent Application No. 05 736 963.3

* cited by examiner

*Primary Examiner* — Leszek Kiliman
(74) *Attorney, Agent, or Firm* — Oblon, Spivak, McClelland, Maier & Neustadt, L.L.P.

(57) ABSTRACT

A molded article containing a powder and a fibrous material which is obtained by a wet papermaking process. The fibrous material has a fiber length frequency distribution such that 30% to 90% of the fibrous material have a fiber length of 0.4 to 2.0 mm and that 9% to 50% of the fibrous material has a fiber length of 0.4 mm or less. The molded article contains at least 50% by weight of the powder.

7 Claims, 2 Drawing Sheets

ARTICLE FORMED INTO SHEET, METHOD FOR PRODUCING THE SAME AND EXOTHERMIC FORMED ARTICLE

TECHNICAL FIELD

The present invention relates to a molded article containing a powdered material and a fibrous material which is obtained by papermaking technique, a method of making the molded article, and a heat-generating molded article.

BACKGROUND ART

Known techniques pertinent to a heat-generating sheet making use of heat generation accompanying oxidation of oxidizable metal powder with air oxygen include the heat-generating element of sheet form described in Japanese Patent 2572612. The heat-generating element of sheet form is made by a papermaking technique using a composition comprising iron powder, activated carbon, an electrolyte, water, and a fibrous material. The heat-generating element of sheet form is produced by suspending a fibrous material in water, adding iron powder, activated carbon, an electrolyte etc. to the suspension to prepare a stock slurry, converting the stock slurry into a wet sheet by papermaking processing, dewatering the sheet by suction, followed by press forming to reduce the water content to 5% to 65% by weight.

According to the technique disclosed, the solid matter of the slurry such as iron powder and activated carbon, particularly iron powder with a high specific gravity and activated carbon with a large specific surface area have poor fixability on the fibrous material when converted into a sheet form. Such solid matter is apt to be sucked together with water without being held to the fibrous material, which has resulted in a failure to obtain a heat-generating element having increased iron powder and activated carbon contents. That is, the retention was poor.

In order to secure a high filler retention, papermaking technology called "dual polymer system" has been practiced, in which two kinds of flocculants are used in combination to form firm flocks of fibers and filler (see Teruo Watanabe, Polyion Complex—Budomari System no Jisso Keiken, Japan Pulp Paper, Vol. 52, No. 12, pp. 1717-1725 (December 1998), Japan Pulp Paper Research Institute). Examples of known dual polymer systems include a combination of cationic starch and colloidal silica, a combination of cationic polyacrylamide and modified bentonite, a combination of polyethylene oxide and a special phenolic resin, and a combination of anionic polyacrylamide and cationic polyacrylamide.

The dual polymer system is a well-known flocculation technique, in which a negatively charged fiber or filler is electrically neutralized with a salt or a low molecular weight cationic polymer to form soft flocks, and a high molecular weight anionic polymer then crosslinks between the fiber and filler to make hard flocks resistant to mechanical outer forces.

When the dual polymer system is followed, however, it is necessary to form strong and large flocks to achieve a high retention. Although an increase of retention is expected, the resulting sheet tends to have a poor formation, leading to fall-off of the filler and non-uniformity in mechanical strength. Further, the wet paper layer tends to be difficult to separate from a papermaking wire. As a result, the stock components are liable to remain on the wire, or the wet paper layer is apt to break when transferred from the wire to a drier, which makes continuous papermaking difficult.

If the size of the flocks is made smaller to prioritize proper papermaking, the formation is improved, but resulting in low retention and poor productivity.

DISCLOSURE OF THE INVENTION

An object of the present invention is to provide a molded article and a method of making the same which are free from various drawbacks associated with the above-described related art and to provide a heat-generating molded article.

The present invention accomplishes the above object by the provision of a molded article containing a powder and a fibrous material which is obtained by a wet papermaking process. The length frequency distribution of the fibrous material is such that 30% to 90% of the fibrous material have a fiber length of 0.4 to 2.0 mm and that 9% to 50% of the fibrous material has a fiber length of 0.4 mm or less. The molded article contains at least 50% by weight of the powder.

The present invention also provides a heat-generating molded article having the molded article of the invention impregnated with an electrolyte solution.

The present invention also provides a method of producing a molded article by a wet papermaking process using a slurry composition prepared by adding a cationic flocculant and an anionic flocculant to a slurry system containing a powder, a fibrous material, and water. The slurry composition is prepared by first adding either the cationic flocculant or the anionic flocculant to the slurry system to make the slurry system bear an excessive amount of charge and then adding the anionic flocculant or the cationic flocculant to the slurry system to neutralize the charge of the slurry system.

The present invention also provides a method of producing a molded article by a wet papermaking process using a slurry composition containing a powder, a fibrous material, a cationic flocculant, ad an anionic flocculant. The anionic flocculant is a carboxymethyl cellulose salt having a degree of etherification of 0.6 to 1.5 and a 1% viscosity of 100 to 4000 mPa·s.

DETAILED DESCRIPTION OF THE INVENTION

The molded article of the present invention will be described with reference to its preferred embodiment, in which the invention is applied to a precursor or intermediate for a heat-generating molded article utilizing an exothermic reaction with oxygen.

The molded article according to the present embodiment contains a fibrous material and a powder as solid matter. The molded article contains the powder in a proportion of at least 50% by weight, more preferably 65% by weight or more, even more preferably 80% by weight or more. With the powder being present in such a preferred proportion, the molded article sufficiently exhibits the characteristics possessed by the powder. The higher the powder content, the more preferred the product. Taking into consideration, however, strength necessary to maintain processability of the resulting molded article, the upper limit of the powder content is about 99% by weight.

The molded article of the present embodiment contains an oxidizable metal and a moisture retaining agent as the powder component.

Any oxidizable metal commonly used in this type of heat-generating molded articles can be used with no particular limitation. Examples of the oxidizable metal include iron powder, aluminum powder, zinc powder, manganese powder, magnesium powder, calcium powder and etc. Iron powder is preferred of them for its handling properties, safety, and production cost. From the standpoint of fixability to a fibrous material and ease of reaction control, it is preferred to use an oxidizable metal powder having a particle size of 0.1 to 300 µm. The term "particle size" as used herein means an in-situ maximum length of powder particles or an average particle size as measured by the dynamic light scattering method, laser diffraction method, and so forth. From the same standpoint, it is preferred to use a powder containing particles having a particle size of 0.1 to 150 µm in a proportion of 50% by weight or more. On the other hand, an oxidizable metal having a fibrous form includes steel wool and etc. An oxidizable metal having a fibrous for preferably has a fiber length of 0.1 to 50 and a thickness of 1 to 1000 µm in view of molding properties and the mechanical strength, surface smoothness and heat-generating performance of the resulting sheet.

The proportion of the oxidizable metal in the molded article is preferably 10% to 95% by weight, more preferably 30% to 80% by weight. With the oxidizable metal proportion falling in the preferred range, the resulting heat-generating molded article heats up to an adequately high temperature, the heat generation lasts for an adequately long period of time, and the article is prevented from getting harder with heat generation. The oxidizable metal content in the molded article can be determined by ash content measurement in accordance with JIS P8128 or with a thermogravimetric analyzer. Vibrating sample magnetization measurement is useful in the case of iron powder, of which the magnetization on applying an external magnetic field is made use of.

Any moisture retaining agent commonly employed in heat-generating molded articles of this type can be used with no particular limitation. The moisture retaining agent not only serves for moisture retention but functions as an agent for holding and supplying oxygen to the oxidizable metal. Examples of preferred moisture retaining agents include activated carbon palm shell charcoal, wood charcoal, bituminous coal, peat, and lignite), carbon black, acetylene black, graphite, zeolite, pearlite, vermiculite, silica, cancrinite, fluorite and etc. Preferred of them is activated carbon for its moisture retaining ability, oxygen supplying ability, and catalytic ability. It is preferred to use a particulate moisture retaining agent having a particle size of 0.1 to 500 µm, particularly the one containing particles with a particle size of 0.1 to 200 µm in a proportion of 50% by weight or more, in view of the capability of providing an effective contact with the oxidizable metal. Moisture retaining agents of other forms are also usable. For example, those of fibrous forms such as activated carbon fiber and etc. can be used.

The moisture retaining agent is preferably present in the molded article in an amount of 0.5% to 60% by weight, more preferably 1% to 50% by weight. With the moisture retaining agent content being within that range, the molded article can hold an adequate amount of water for heat generation, the molded article can reach a sufficiently high temperature, the moisture retaining agent hardly falls off, and the molded article has sufficient mechanical strength such as flexural strength and tensile strength.

The fibrous material should be a material that can be converted into a sheet form by wet papermaking processing. Examples of the fibrous material include natural organic fibers and synthetic organic fibers. The natural organic fibers include plant fibers, animal fibers and etc. Examples of plant fibers are cotton, kapok fiber, wood pulp, non-wood pulp, peanut protein fiber, corn protein fiber, soybean protein fiber, mannan fiber, rubber fiber, hemp, Manila fiber, sisal fiber, New Zealand flax, Luo Buma, coconut, rush, straw and etc. Examples of animal fibers are wool, goat hair, mohair, cashmere, alpaca, angora, camel, vicuna, silk, down, small feather, alginate fiber, chitin fiber, casein fiber and etc. The synthetic organic fibers include semi-synthetic ones, such as cellulose diacetate, cellulose triacetate, oxidized cellulose acetate, promix, chlorinated rubber, rubber hydrochloride and etc. Also useful are single-component fibers made of polyolefin (e.g., high-density polyethylene, medium-density polyethylene, low-density polyethylene, polypropylene or etc.), polyester, polyvinylidene chloride, starch, polyvinyl alcohol, polyvinyl acetate, or a copolymer thereof, or a modified product thereof, and sheath/core conjugate fibers having the above-recited resin component as a sheath. Of these fibers, polyolefin fibers and modified polyester fibers are preferably used for high bonding strength between individual fibers, high ability to form a three-dimensional network structure on fusion bonding of individual fibers, and a lower melting point than the ignition point of pulp fiber. Synthetic fibers of polymers having branches, such as branched polyolefin fibers or etc., are also preferred for their fixing capabilities for the oxidizable metal and the moisture retaining agent. The above-recited fibrous materials can be used either individually or as a combination of two or more thereof. Recycled products of these fibrous materials are also employable. Among the fibers recited, particularly preferred are wood pulp (e.g., LBKP, NBKP, used paper pulp and etc) and cotton in view of their fixing capabilities for the oxidizable metal and the moisture retaining agent, flexibility of the resulting molded article, oxygen permeability of the molded article owing to the presence of interstitial voids, and the cost of production.

Figure 1:
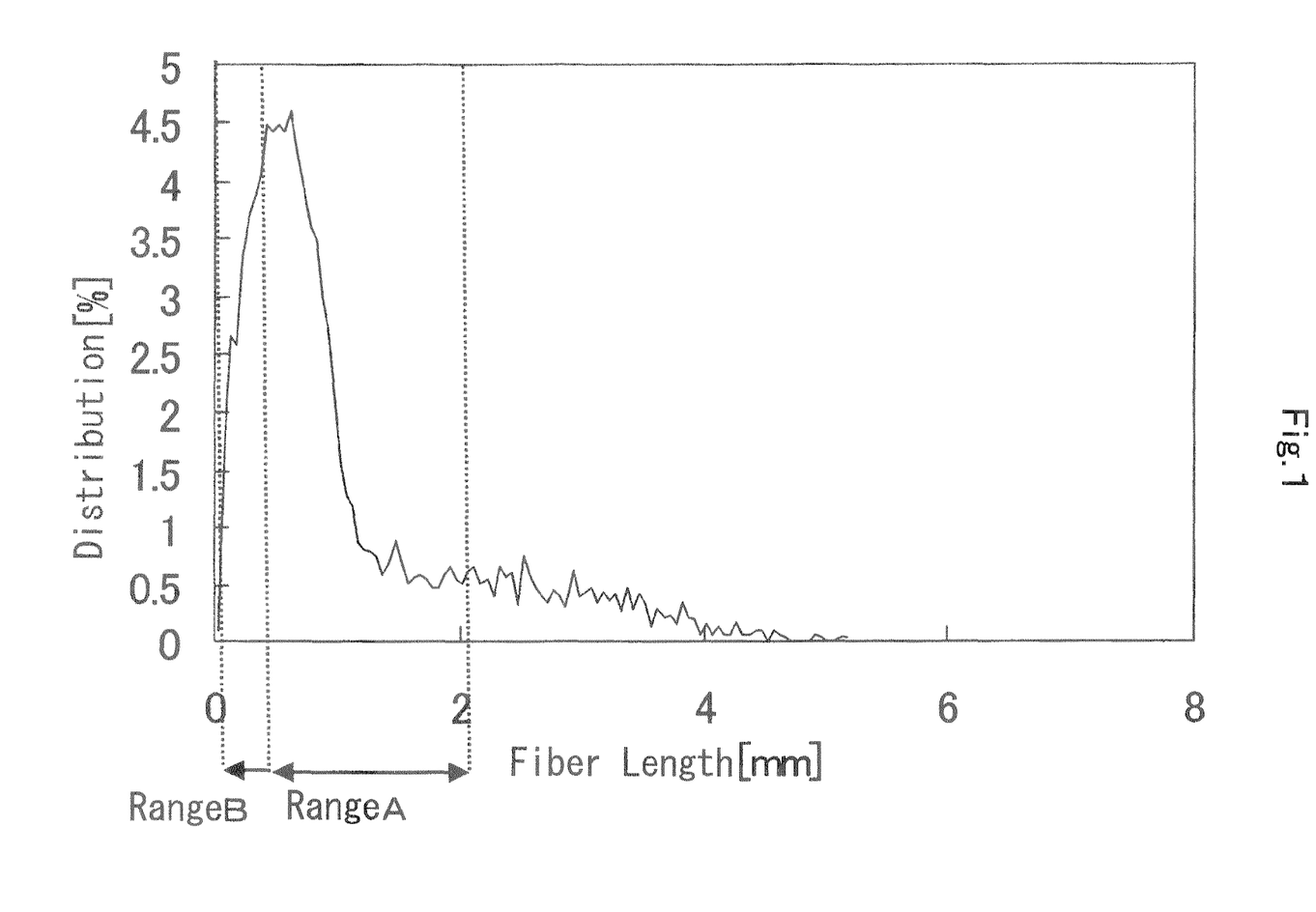
FIG. 1 is a graph showing the fiber length frequency distribution of the fibrous material.

In the manufacture of a molded article by wet papermaking processing, there has been a problem that part of a powdered material (solid matter) in a stock slurry is suction-drained with water without being fixed onto a fibrous material, resulting in a poor filler retention. As a result of the present inventors' study aiming to solve the problem, they have found that using fibers with a relatively short length brings about increased fixing capability for the water retaining agent but, in turn, results in reduction of mechanical strength of the molded article. In order to satisfy these conflicting characteristic requirements, the inventors have continued extensive investigations. As a result, it has been revealed to be effective to use a fibrous material having a fiber length frequency distribution such that 30% to 90% of the fibrous material have a fiber length of 0.4 to 2.0 mm (this range of fiber length will hereinafter be referred to as range A) and that 9% to 50% of the fibrous material has a fiber length of 0.4 mm or less (this range of fiber length will hereinafter be referred to as range B). An exemplary fiber length frequency distribution of a fibrous material that is preferably used in the molded article of the invention is shown in FIG. 1. In the frequency distribution curve, the ratio of the area within the range A to the total area is equal to the proportion (%) of the fibrous material having a fiber length within the range A. Likewise, the ratio of the area within the range B to the total area is equal to the proportion (%) of the fibrous material having a fiber length within the range B. Using a fibrous material having such a frequency distribution effectively prevents solid matter from draining off in the step of papermaking thereby allowing for production of a molded article with high retention and sufficiently high mechanical strength. To further ensure the improvement of these characteristics, the proportion of the fibrous material with a fiber length of the range A is preferably 40% to 80%, more preferably 45% to 75%, and the proportion of the fibrous material with a fiber length of the range B is preferably 10% to 40%, more preferably 11% to 35%.

Fiber length frequency distribution and an average fiber length (described infra) were measured from length-weighted values calculated with a fiber length analyzer KAJAAANI FS-200 available from Valmet Automation Inc. As a condition of measurements, the fiber count was 20,000 or more.

The fibrous material inclusive of the fibrous material with a fiber length of the range A and the fibrous material with a fiber length of the range B preferably has a length-weighted average fiber length (hereinafter simply referred to as an average fiber length) of 0.3 to 2.0 mm, more preferably 0.5 to 1.8 mm, from the viewpoint of mechanical strength, high retention during papermaking, and compositional stability of the molded product. The average fiber length is obtainable as a length-weighted average obtainable from a fiber length frequency distribution of the fibrous material. A length-weighted average is calculated from $\Sigma N_i l_i^2 / \Sigma N_i l_i$, where $l_i$ represents a fiber length; and $N_i$ represents the number of fibers.

It is preferred for the fibrous material to have a CSF (Canadian Standard Freeness) of 600 cc or less, more preferably 300 cc or less, even more preferably 100 cc or less, to have ensured fixing capabilities for powdered components and to provide a molded article with further improved mechanical strength.

A fibrous material satisfying the above-mentioned requirements, i.e., fiber length frequency distribution, average fiber length, and freeness can be obtained by selecting, for example, the kind (from, e.g., NBKP, LBKP, used paper pulp and etc.), beating conditions, or conditions of blending two or more kinds of fibers. From the perspectives of mechanical strength, retention during papermaking, and compositional stability of the molded article, it is particularly preferred to use a blend of relatively long pulp fibers having an average fiber length of 1.5 to 2.5 mm and relatively short pulp fibers having an average fiber length of 0.3 to 1.0 mm at a blending ratio of 30/70 to 70/30 by weight.

The fibrous material preferably has negative surface charges. A fibrous material having stronger negative charges on its surface has higher ability to fix the powder components including the oxidizable metal, the moisture retaining agent and the like thereby to hold more amounts of the powdered components to provide a molded article with higher performance in heat generation and deoxidization. Running of large quantities of the powder components into drain water can be reduced, which is favorable for the productivity and environmental protection.

The amount of charge of the fibrous material is preferably $-2.5 \times 10^{-6}$ eq/g or under, more preferably $-40 \times 10^{-6}$ eq/g or under, so as to further improve the retention of the molded article.

The amount of charge of the fibrous material is measured by colloid titration. In detail, ten grams of a 0.4 wt % slurry of the fibrous material is analyzed with a particle charge detector PCD03 from Mutec, and the amount of charge as measured is divided by the weight of the fibrous material. The slurry to be analyzed was prepared using ion exchanged water.

The amount of surface charge is also determined from zeta potential, an apparent potential at the shear plane separating a charged particle and a solution, which can be measured by streaming potential measurement or electrophoresis measurement.

The fibrous material content in the molded article is preferably 2% to 50% by weight, more preferably 5% to 40% by weight. This range is advantageous for fixing the oxidizable metal and the moisture retaining agent to achieve improved retention, preventing the molded article from getting brittle, and obtaining desired heat generating performance.

The fibrous material content and the oxidizable metal content in a molded article can be measured with, for example, a thermogravimetric analyzer. Subtracting these contents from the total weight gives the content of the moisture retaining agent.

The molded article can contain a flocculant as hereinafter described. If desired, the molded article can contain any additives commonly used in papermaking such as sizes, colorants, strengthening agents, retention aids, loading materials, thickeners, pH control agents, and bulking agents, with no particular limitation. The amounts of the additives to be added can be decided as appropriate to the kinds.

Where the molded article has a sheet form, the thickness of the molded article is preferably 0.08 to 1.2 mm, more preferably 0.1 to 0.6 mm, to assure sufficient heat-generating performance and mechanical strength.

When the molded article has a sheet for, the basis weight of the molded article is preferably 10 to 1000 m$^2$, more preferably 50 to 600 g/m$^2$, in view of the stability in sheet formation by wet papermaking while avoiding reduction in usability.

A preferred embodiment in which the molded article of the present invention is applied to a heat-generating molded article will then be described. Where the molded article of the present invention is a heat-generating molded article, the above-described molded article contains an electrolyte and is impregnated with water. The electrolyte to be added can be of any kind chosen from those commonly used in this type of heat-generating molded articles. Examples of useful electrolytes include sulfates, carbonates, chlorides or hydroxides of alkali metals, alkaline earth metals or heavy metals. Preferred of them are chlorides, such as sodium chloride, potassium chloride, calcium chloride, magnesium chloride, and iron (I) or (II) chloride, for their electroconductivity, chemical stability, and low production cost. These electrolytes can be used either individually or as a combination of two or more thereof.

To obtain desired heat-generating performance and prevent precipitation of an excess electrolyte, the amount of the electrolyte in the heat-generating molded article preferably ranges from 0.05% to 8% by weight, more preferably 0.1% to 6% by weight, based on the molded article before incorporation of the electrolyte and water. The water content of the heat-generating molded article preferably ranges from 5% to 80%, more preferably 10% to 60% by weight, based on the molded article before incorporation of the electrolyte and water to secure a sufficient water content to sustain oxidation reaction, obtain desired heat-generating performance, and prevent reductions in shape retention and mechanical strength of the molded article.

The temperature reachable by heat generation can freely be designed by the formulation of the components according to the purpose, that is, whether a steep temperature rise is desired or a long duration of heat-generating reaction at a relatively low temperature is desired, and the like. The temperature reached by the heat-generating molded article is preferably 30° to 100° C., more preferably 35° to 90° C. Similarly, the heat-generating molded article can be designed to generate an arbitrary amount of water vapor. It is desirable for the heat-generating molded article to generate 50 to 1000 mg, more preferably 100 to 600 mg, of water vapor.

The amount of water vapor generated is measured as follows. A 50 mm side square test piece cut out of a heat-generating molded article is sealed in between a moisture permeable sheet having a water vapor transmission rate (JIS Z208) of 5000 g/(m²·24 hr) and a moisture impermeable sheet to make a closed bag. A tester having a 4.2-liter closed chamber adjusted to 1% RH or less in which 2.1 l/min of dry air is fed is prepared. The bag containing the test piece is placed in the chamber with the moisture permeable sheet side up and let to heat up. The humidity of the air discharged out of the chamber is measured with a hygrometer, from which the amount of water vapor generated per unit time after the start of heat generation is calculated according to equation (1) shown below. The cumulative amount of water vapor generated for a period of 10 minutes is obtained and converted to a value per unit time. In the following equations, e stands for water vapor pressure (Pa); es, a saturated water vapor pressure (Pa; according to JIS Z8806); T, temperature (° C.; dry-bulb temperature); and s, sampling cycle (sec).

Relative humidity $U(\% RH) = (e/es) \times 100$

Absolute humidity $D(g/m^3) = (0.794 \times 10^{-2} \times e)/(1 + 0.00366T) = (0.794 \times 10^{-2} \times U \times es)/[100 \times (1 + 0.00366T)]$ Unit air volume $P$ (liter) $= (2.1 \times s)/60$ Amount of water vapor per unit time $A(g) = (P \times D)/1000$     (1)

A preferred method of producing the above-described molded article and heat-generating molded article will be described with reference to production of products of sheet form.

The production starts with preparation of a slurry composition containing the oxidizable metal, the moisture-retaining agent, the fibrous material, and water (hereinafter sometimes referred to as a slurry system), to which flocculants are to be added. The slurry composition is prepared by adding these components to water. Taking into consideration the retention and the fixability of powder components especially the fixability of an oxidizable metal having a high specific gravity, they are preferably added in this order: the fibrous material, the oxidizable metal, and the moisture retaining agent. More specifically, powders having a larger surface area or a higher specific gravity than the fibrous material are added before the fibrous material to be fixed better.

The total concentration of the oxidizable metal and moisture retaining agent in the slurry before addition of a flocculant and before being fed to a paper machine is preferably 1.5% to 20% by weight, more preferably 3% to 15% by weight. The concentration of the fibrous material is preferably 0.075% to 10% by weight, more preferably 0.15% to 7.5% by weight. Within these concentration ranges, separation and sedimentation of the powder components from the fibrous material are suppressed, and adsorbability of other components onto the fibrous material and powder is improved, whereby improvement of retention and stabilization of the compositional ratio can be accomplished. The slurry prepared is then diluted with water at a desired dilution and transferred to a papermaking step where it is converted to a molded article.

A flocculant is added to the slurry. Examples of the flocculant include inorganic ones, such as metal salts, e.g., aluminum sulfate, polyaluminum chloride, iron (III) chloride, polyferric sulfate, iron (II) sulfate and etc.; polymeric ones, such as polyacrylamides, sodium polyacrylates, Mannich base-modified polyacrylamides, aminoalkyl poly(meth)acrylates, sodium carboxymethyl celluloses, potassium carboxy ethyl celluloses, ammonium carboxymethyl celluloses, chitosans, starches, polyamide-epichlorohydrins and etc., organic coagulants, such as dimethyldiallylammonium chloride type or ethyleneimine type alkylene dichloride-polyalkylenepolyamine condensates, dicyandiamide-formalin condensates and etc.; clay minerals, such as montmorillonite and bentonite; silicon dioxide and its hydrates, such as colloidal silica; and hydrous magnesium silicate, such as talc or the like. The flocculants can be used either individually or as a combination of two or more thereof.

In particular, use of a combination of an anionic flocculant and a cationic flocculant is preferred for the following reason. The combined flocculants form small and firm flocks in the slurry immediately before it reaches a paper machine. The flocks retard settlement of the powder components and suppress separation and settlement of the powder components from the fibrous material, which is effective in improving sheet surface properties, formation, molding properties, properties of fixing the solid matter including the oxidizable metal, the moisture retaining agent and etc., sheet strength and the like.

With respect to the combined use of an anionic flocculant and a cationic flocculant, the present inventors have ascertained that the following strategy of addition of flocculants results in the production of a molded article (sheet) excellent in retention, stability of compositional ratio, and quality such as formation. That is, in a first stage of addition, either one of the cationic flocculant or the anionic flocculant is added to bring the slurry system into an excessively positively or negatively charged state. Then, in a second stage of addition, the other of the flocculants is added to put the charges of the slurry system into a neutralized state. The term "neutralized state" as used herein means that the amount of the charge of the slurry system is in the range of from $-2.0 \times 10^{-7}$ to $+2.0 \times 10^{-7}$ eq/g as will be described later. The term "excessively (positively or negatively) charged state" as used herein means a state that is not in a neutralized state.

The inventors have analyzed the mechanism of effects of addition of the aforementioned flocculants to reveal the following facts. When a slurry system is turned into an excessively charged state, fibrils, i.e., small fibers of the fibrous material in the slurry system spread sufficiently to exhibit enhanced capabilities to capture powders. After such a state of the fibrous material is achieved, the charges of the slurry system are brought into a neutralized state, whereby the powder components are stably and firmly fixed on the fibrous material. As a result of further studies, they have also ascertained the following preferences. It is preferred that each of the flocculants be added in a continuous manner into a transit tank or a pipe rather than batchwise into a tank in view of stability of the flocks with time. It is more preferred that the flocculants be added to the slurry while it is in a pipe. It is also preferred that an agitator, such as a static mixer, be disposed between two positions for adding the two kinds of flocculants to form more uniform and more stable flocks and thereby to provide a sheet with vary high quality. Furthermore, it is preferred, the inventors have found, that addition of a cationic flocculant be followed by addition of an anionic flocculant to further ensure fixing of the powder components on the fibrous material.

For example, two kinds of flocculants, a cationic flocculant A and an anionic flocculent B, may be added in three positions in this way: the cationic flocculant A is first added to bring the slurry system into an excessively (positively)

charged state, the anionic flocculant B is then added to bring the slurry system into an excessively (negatively) charged state, and the cationic flocculent A is finally added to bring the charges into a neutralized state. When addition is made in three or more positions, the kinds of the cationic or anionic flocculants that are added twice or more times may be the same or different. The cationic or anionic flocculant may be added in combination with a nonionic flocculant.

From the standpoint of formation of the molded article, fixability of the powder, and stability of flock strength, the absolute value of the amount of charge of the slurry system after the first stage of addition is preferably $3 \times 10^{-7}$ to $50 \times 10^{-7}$ eq/g, more preferably $3 \times 10^{-7}$ to $30 \times 10^{-7}$ eq/g even more preferably $3 \times 10^{-7}$ to $20 \times 10^{-7}$ eq/g.

The amount of charge of a slurry system during the preparation of a slurry composition is a value obtained by filtering a slurry having a solid concentration of 7.5% by weight through filter paper (ADVANTEC 26, ANANASHI type available from Toyo Roshi Kaisha, Ltd.), analyzing a 10 g portion of the filtrate on a particle charge detector (PCD03 from Mutec), and dividing the amount of charge as measured by the weight of the filtrate. The slurry to be analyzed was prepared using ion exchanged water.

From the standpoint of formation of the molded article, fixability of the powder, and stability of flock strength, the ratio of the absolute amount of charge of the slurry system after the first stage of addition to that before the first stage of addition (the ratio will hereinafter be referred to as a charge ratio) is preferably 3 to 500, more preferably 3 to 300, even more preferably 3 to 100.

In making a heat-generating molded article, in particular, the charge ratio is preferably 30 to 150, more preferably 30 to 100, in view of retention and stability of flock strength with time.

Examples of the anionic flocculant include inorganic ones, such as bentonite, colloidal silica, combinations thereof and etc., and polymeric ones, such as polyacrylamides, sodium polyacrylates, carboxymethyl cellulose salts, combinations thereof and etc. Examples of the cationic flocculant include inorganic ones, such as polyaluminum chloride, ammonium sulfate, combinations thereof and etc., and polymeric ones, such as polyacrylamides, polyamines, polyethylene-imines, starches, chitosans, polydiallyldimethylammonium chlorides, polyamide-epichlorohydrins, combinations thereof, and etc. Suitable anionic/cationic flocculants combinations include a combination of colloidal silica or bentonite (anionic) and starch or polyacrylamide (cationic) and a combination of sodium carboxy ethyl cellulose (anionic) and polyamide-epichlorohydrin (cationic).

In particular, it is preferred that the carboxymethyl cellulose salt have a degree of etherification of 0.6 to 1.5, more preferably 0.8 to 1.5. Within the etherification degree, the anionic groups have increased adsorbing properties, which is advantageous for forming a polyionic network with cationic groups. It is also preferred for the carboxymethyl cellulose salt to have a 1% viscosity of 100 to 4000 mPa·s, more preferably 400 to 3500 mPa·s, to form a polyionic network thereby forming flocks having strength withstanding mechanical shear force as well as high stability. The 1% viscosity is a value measured with a Brookfield viscometer.

The amount of the flocculants to be added is preferably 0.01% to 5% by weight, more preferably 0.05% to 1% by weight, based on the solids content of the slurry from the standpoint of fixing capabilities for the solid matter including the oxidizable metal and the moisture retaining agent and stable production of a molded article.

From the viewpoint of stably fixing the powder components to the fibrous material to improve retention and securing stability in continuous papermaking, the amount of charge of the slurry system in a neutralized state is preferably $-2.0 \times 10^{-7}$ to $+2.0 \times 10^{-7}$ eq/g, more preferably $-1.5 \times 10^{-7}$ to $1.5 \times 10^{-7}$ eq/g.

From the same viewpoint as for the amount of charge of the slurry system in a neutralized state, a reduction with time of flock strength in the slurry system is preferably 0% to 60%, more preferably 0% to 50%.

Figure 2:
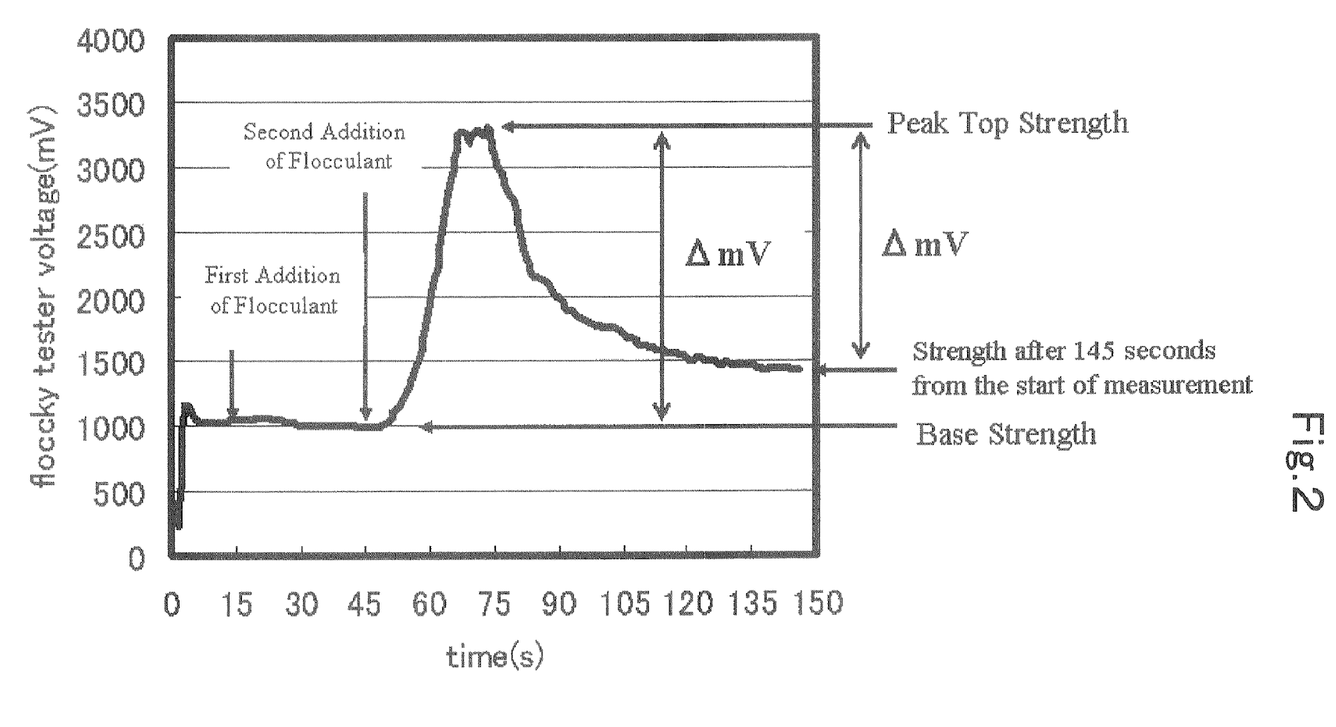
FIG. 2 is a diagram showing the method of calculating reduction in flock strength with time.

A lower reduction of flock strength with time means higher strength of the flocks against outer force. A reduction with time of flock strength is a measure of how stably the slurry system can be converted into sheet without involving flock destruction under any outer force in an actual paper machine. A reduction of flock strength with time can be measured using Floccky Tester ODA-10 available from Koei Industry Co., Ltd. A flocculant is added to a slurry having a solids concentration of 7.5% by weight while stirring at 120 rpm to form flocks, and changes in voltage output of the Floccky tester are plotted to measure flock strength. As depicted in FIG. 2, a first flocculant is added 15 seconds from the start of measurement, and a second flocculant is added 30 seconds from the addition of the first flocculent, followed by further stirring the slurry. A reduction with time of flock strength is calculated from the flock strength measured after the rotation is continued for 100 seconds after the second addition (the strength after 145 seconds from the start of measurement) and the peak top value according to the following equation. Each of the flocculants is added over a period of about 5 to 10 seconds.

Reduction with time of flock strength in slurry system=teak top strength–strength after 145 seconds from the start of measurement)/(peak top strength–base strength)×100

The flock strength at a given time of measurement corresponds to the voltage output of Floccky Tester.

The thus prepared slurry composition is converted into a molded article of sheet form by wet papermaking. To carry out wet papermaking, continuous paper machines, such as cylinder paper machines, foundrinier paper machines, short-wire paper machines, twin-wire paper machines and the like, are used. Papermaking may be carried out manually in a batch mode. A multilayer molded article may be obtained by using the above-described slurry composition and a slurry composition having a different formulation. A multilayer molded article may be obtained by laminating molded sheets separately prepared from the same slurry composition or laminating a molded sheet prepared from the composition and a molded sheet prepared from a composition having a different formulation. In the present invention whatever method is adopted, use of the fibrous material having the aforementioned fiber length frequency distribution secures satisfactory fixation of solid matter, such as the oxidizable metal and moisture retaining agent, to provide a molded article at a high filler retention.

The molded article (wet web) is dewatered preferably to a water content of 70% by weight or less, more preferably 60% by weight or less, for assuring shape retention and mechanical strength after papermaking. Dewatering is carried out by, for example, suction, application of pressurized air, or pressing under a pressure roll or a pressure plate, or the like.

The molded article is then positively dried to remove the water content thereby to inhibit oxidation of the oxidizable metal during the subsequent steps and to provide an article having excellent long-term storage stability. Drying the molded article is advantageous in that fixation of the oxidizable metal and the moisture retaining agent on the fibrous material is ensured to prevent their falling off the sheet and that improvement in mechanical strength by addition of a heat fusible component or a thermal crosslinking component may be expected.

The means for drying the molded article is selected appropriately depending on the sheet thickness, the treatment given to the sheet before drying, the water contents before and after the drying, and the like. Useful drying means include contact with a heating structure (heat generating element), application of heated air or stream (superheated steam, vacuum drying, microwave heating, and ohmic heating. The drying may be carried out simultaneously with the above-described dewatering.

Shaping of the molded article (inclusive of sheet formation, dewatering, and drying) is preferably conducted in an inert gas atmosphere. Nevertheless, because the molded article in this stage is free from an electrolyte acting as an oxidation promoter, the shaping may be performed in an ordinary air atmosphere if desired, which allows for simplification of equipment. Where necessary, the dried sheet is fabricated by craping, slitting, trimming or any other processings for shaping or forming. Thin and yet tearproof, the resulting molded article can be taken up in a roll if needed. The molded article or a plurality of the molded articles, either alone or as laminated with other film or sheet (e.g., paper, woven fabric, nonwoven fabric or plastic film), may be pressed, embossed or needle-punched to be united into a unitary sheet, given uneven patterns or perforated. In order to facilitate heat sealing for lamination or other processing, a thermoplastic resin component or a hot-water-soluble component may be incorporated into the slurry.

An electrolyte and water are then incorporated into the resulting molded article to obtain a heat-generating molded article. This step is preferably carried out in an inert gas atmosphere such as nitrogen or argon. Where the electrolyte is incorporated by impregnation with an aqueous electrolyte solution, the impregnating step can be conducted in an ordinary air atmosphere because oxidation that may proceed immediately after the impregnation is mild.

The method of incorporating an electrolyte into the molded article is selected as appropriate to the treatment given to the article after sheet formation, the water content and the form of the article, and the like. For example, the electrolyte can be incorporated by impregnating the molded article with an aqueous solution having a prescribed electrolyte concentration, or adding a powdered electrolyte having a prescribed particle size directly to the molded article. Impregnation with an aqueous electrolyte solution having a prescribed concentration is preferred for achieving uniform distribution of the electrolyte and simultaneously controlling the water content of the resulting article.

When an electrolyte is incorporated into the molded article by impregnation with an aqueous solution of the electrolyte, the manner of impregnation is chosen as appropriate to the form (e.g., thickness) and the water content of the molded article. Impregnation methods include spraying, syringing into part of the molded article (the injected electrolyte solution penetrates throughout the article by capillarity of the fibrous material), coating with a brush, etc., soaking in the aqueous solution, gravure coating, reverse coating, doctor blade coating, and so forth. Spraying is preferred for uniform distribution, ease of operation, and relatively low cost of equipment. Where the finished product has a complicated shape or layer structure, syringing is preferred for productivity, process flexibility (the final finishing process can be done in a separate step), and simplicity of equipment. It is possible to conduct syringing after the molded article is enclosed in a container, for example, an oxygen-permeable holder.

Where necessary, the water content of the molded article containing the electrolyte is adjusted to provide a stabilized heat-generating molded article. If desired, the heat generating molded article thus prepared can be fabricated by trimming into a prescribed size or stacked one on top of another. A stack of the heat-generating molded article may be united together by embossing.

The resulting heat-generating molded article is then covered with an oxygen permeable covering layer. The covering layer may have oxygen permeability over the entire area or only a selected area thereof. The covering layer is not particularly limited in material as long as it has air permeability. For example, paper, nonwoven fabric, a finely porous membrane, a finely perforated resin film or the like is superposed on the heat-generating molded article to provide a covering layer. Otherwise, a synthetic resin coating, an emulsion coating, or a like coating may be infiltrated into or applied to the heat-generating molded article to form a covering layer.

The heat and water vapor generation characteristics of the heat-generating molded article can be controlled as desired by controlling the oxygen permeability of the covering layer. Moisture permeability is used as a measure of oxygen permeability. Using a covering layer with high moisture permeability provides a heat-generating molded article that heats up to a high temperature and comes to release much water vapor in a short time. Choosing a covering layer with low moisture permeability provides, on the other hand a heat-generating molded article that sustains heat generation for an extended period of time with mild water vapor generation.

The heat-generating molded article thus obtained is supplied as sealed in an oxygen impermeable and moisture impermeable package until use.

The heat-generating molded article according to the present embodiment is not only suited for use as an ultrathin heat pack body warmer but applicable to a variety of uses with its heat generating function and water vapor generating function combined with various functional preparations. For instance, the heat-generating molded article is combined with functions for cleaning, sterilization, slow wax release, scenting or deodorization to provide preparations for home care applications (cleaning or treatment of flooring, tatami, kitchen stoves and fans, etc.), air care applications to create a comfortable ambience, car care applications (cleaning and waxing), facial and body skin care applications (cleansing, sterilizing moisturizing, removal of sebum, removal of dark circle in eye area, line smoothing, and removal of dullness), and health care applications (to be wrapped around or applied to the neck, a shoulder, the lower back, a hand, a foot, etc. to alleviate pains or period pains). When combined with a pack, the heat-generating molded article provides a skin-care hot pack for moisturizing, eliminating darkness under the eye, wrinkles or skin dullness, an eye-care hot pack for eliminating eyestrain or improving eyesight, a pack for preventing a cold or alleviating sore throat, or a steamy mask for protection from pollen. When combined with cataplasm, the heat-generating molded article provides health-care hot cataplasm for alleviating pains in the neck, shoulders, feet, the lower back, etc. or period pains. The heat-generating molded article combined with a hair cap is useful as a warming cap for hair care applications in permanent waving, hair dyeing or hair growth promotion. The heat-generating molded article can be incorporated into a mitten-shaped article or a sock-shaped article for use in hand care applications or foot care applications. The heat-generating molded article can have a shape with projections and depressions to provide an article like a warming brush. The heat-generating molded article is also useful for bake-out applications to remove harmful substances such as formalin, adhesive applications to thermally accelerate curing, warming or heating applications in packaging or distributing foods and commodities, emergency applications such as emergency clothing and blankets, and for medical applications such as warming bandage. Making use of oxidation reaction, the heat-generating molded article of the present invention finds other various applications. For example, it is serviceable as an oxygen scavenger for keeping foods fresh, protecting metal against rusting, protecting bedding, clothing, art objects from mould or insects and the like.

The molded article of the invention and the method of the invention for producing a molded article are not limited to the above-described embodiments, and various changes and modifications can be made thereto without departing from the spirit and scope of the present invention.

The molded article of the invention and the method of the invention for producing a molded article are applicable to not only a heat-generating molded article that utilizes an exothermic reaction with oxygen as in the above-described embodiments but also other molded articles containing the above-described fibrous material and various functional powders and the production thereof as follows.

The present invention is applicable to a photocatalytic molded article obtained by wet papermaking from a slurry composition containing the above-described fibrous material, a powdered photocatalyst, such as titanium dioxide, zinc oxide, a combination thereof or etc., a powdered inorganic adsorbent and, if desired inorganic fiber, such as glass fiber, ceramic fiber, a combination thereof or etc. The present invention is also applicable to a molded article for castings obtained by wet papermaking from a slurry composition containing the above-described fibrous material, inorganic fiber such as carbon fiber or glass fiber, and a powder, such as silica, alumina, mullite, magnesia, zirconia, mica, graphite or obsidian. The present invention is also applicable to a molded article having deodorizing function or ethylene gas adsorbing unction which is obtained by wet papermaking from a slurry composition containing the above-described fibrous material and a powder, such as zeolite, sepiolite or etc., a molded article for petroleum or alcohol separation or decomposition which is obtained by wet papermaking from a slurry composition containing the above-described fibrous material and a powder, such as zeolite or etc., a molded article as an oleochemical catalyst which is obtained by wet papermaking from a slurry composition containing the above-described fibrous material, an oxidizable metal powder as an oleochemical catalyst, and inorganic or metallic fiber for securing durability, a molded article obtained by wet papermaking from a slurry composition containing the above-described fibrous material and a magnetic powder, such as magnetite powder, a molded article generating hydrogen through reducing action which is obtained by wet papermaking from a slurry composition containing the above-described fibrous material and iron oxide powder, a molded article serviceable as a carrier of various enzymes which is obtained by wet papermaking from a slurry composition containing the above-described fibrous material and an ion exchange resin powder, a molded article for making a biocomposite which is obtained by wet papermaking from a slurry composition containing the above-described fibrous material and a powder such as apatite powder or etc., and a molded article having a polishing unction which is obtained by wet papermaking from a slurry composition containing the above-described fibrous material and a powdered abrasive, such as calcium carbonate powder or etc.

The description about the heat-generating molded article of the aforementioned embodiment and the fibrous materials, powders and flocculants used in the production of the heat-generating molded article also applies to the above-listed other molded articles. Where in using a functional powder with a relatively small particle size, such as a powdered catalyst to be added is preferably 0.01% to 10% by weight, more preferably 0.05% to 7% by weight, in view of powder fixability and stable molding by papermaking.

The molded article of the present invention can have a shape as appropriate to the powder contained therein. For example, a heat-generating molded article usually has a sheet form as described hereinabove but may have a hollow shape such as a cylinder or a bottle or a container shape such as a caton or a tray. For applications as a catalyst as referred to above, the molded article can have various shapes according to the catalytic reaction including a shape punched out of a sheet, a cylindrical shape, a honeycomb shape as well as a sheet form. The molded article of the present invention may be fused and/or fired to make a fired composite endowed with a desired function.

EXAMPLES

The present invention will now be illustrated in greater detail with reference to Examples, but it should be noted that the invention is not construed as being limited thereto.

In Examples 1 to 10 and Comparative Examples 1 to 3, a molded article was made using each of the fibrous materials having the fiber length frequency distributions and the length-weighted average fiber length shown in Table 1. The retention in papermaking, the composition ratio of the solid content, the powder content, and the tensile strength and heat generation characteristics of the resulting molded article were evaluated as described later. The results of evaluation are shown in Tables 1 and 2. In Examples 11 to 17 and Comparative Examples 4 to 7, the fibrous material of Example 2 was used, and the amount of charge of the slurry system during the preparation of the slurry composition, the retention in papermaking, the composition ratio of the powder content, the formation of the resulting molded article, and the releasability of a wet web from a papermaking wire were evaluated as described later. The results of evaluation are shown in Table 3. In Example 18, a molded article containing a powdered catalytic substance used to prepare an aldehyde through alcohol reaction was made.

Example 1

(1) Formulation of Slurry Composition
Fibrous material: pulp fiber NBKP (Mackenzie (trade name) from Fletcher Challenge Canada, Ltd., CSF: 500 ml; amount of charge: $-3.14 \times 10^{-6}$ eq/g) 15 wt %
Oxidizable metal: iron powder (RKH (trade name) from Dowa Iron Powder Co., Ltd. 75 wt %
Moisture retaining agent: activated carbon (Carboraffin (trade name) from Japan EnbioChemicals, Ltd.) 10 wt %
Flocculant: per 100 parts by weight of the solids content of a slur composition, i.e., the above-recited fibrous material, oxidizable metal, and moisture retaining agent)
Cationic flocculant: polyamide-epichlorohydrin resin (WS4020 (trade name) from Seiko PMC Corp) 0.5 parts
Anionic flocculant: sodium carboxymethyl cellulose (HE1500F (trade name) from Dai-ichi Kogyo Seiyaku Co., Ltd.; degree of etherification: 1.45; viscosity: 2500 to 3500 mPa·s) 0.18 parts Water: industrial water to result in a solid concentration of 3 wt %.

To water were added and dispersed therein the fibrous material, oxidizable metal and moisture retaining agent in the order described. The cationic flocculant was added first. After thoroughly agitating the slurry system, the anionic flocculant was added to prepare a slurry composition.

(2) Papermaking Conditions

The slurry composition thus prepared was diluted to a concentration of 0.5 wt % and converted into a wet web on a 250 mm by 250 mm square sheet machine (available from Kumagai Riki Kogyo, Ltd.) in accordance with JIS P8209.

(3) Drying Conditions

The wet web was dried on a KRK rotary dryer (from Kumagai Riki Kogyo, Ltd.) to a water content of 1 wt % or less to obtain a molded article (a heat-generating molded article precursor).

(4) Electrolyte Addition Conditions

The electrolyte solution shown below was applied to the dried molded article (heat-generating molded article precursor) in an amount of 60 parts by weight per 100 parts by weight of the molded article to obtain a heat-generating molded article.

(5) Electrolyte Solution
  Electrolyte: purified salt (NaCl)
  Water: industrial water
  Concentration: 5 wt %

Example 2

A molded article was prepared in the same manner as in Example 1, except for using pulp fiber having a CSF of 150 ml and a charge quantity of $-3.66 \times 10^{-6}$ eq/g. A heat-generating molded article was obtained in the same manner as in Example 1.

Example 3

A molded article was obtained in the same manner as in Example 1, except for using pulp fiber having a CSF of 65 ml and a charge quantity of $-4.38 \times 10^{-6}$ eq/g. A heat-generating molded article was obtained in the same manner as in Example 1.

Example 4

A molded article was obtained in the same manner as in Example 1, except for using pulp fiber LBKP having a CSF of 300 ml and a charge quantity of $-6.51 \times 10^{-6}$ eq/g (CENIBRA (trade name) from Celulose Nipo-Brasileira S.A.). A heat-generating molded article was obtained in the same manner as in Example 1.

Example 5

A molded article was obtained in the same manner as in Example 1, except for using pulp fiber having a CSF of 130 ml and a charge quantity of $-7.29 \times 10^{-6}$ eq/g. A heat-generating molded article was obtained in the same manner as in Example 1.

Example 6

A molded article was obtained in the same manner as in Example 1, except for using pulp fiber having a CSF of 50 ml and a charge quantity of $-9.94 \times 10^{-6}$ eq/g. A heat-generating molded article was obtained in the same manner as in Example 1.

Example 7

A molded article was obtained in the same manner as in Example 1, except for using a 50:50 blend of the pulp fiber of Example 2 and the pulp fiber of Example 5 as a fibrous material. A heat-generating molded article was obtained in the same manner as in Example 1.

Example 8

A molded article was obtained in the same manner as in Example 1, except for using a 50:50 blend of the pulp fiber of Example 3 and the pulp fiber of Example 6 as a fibrous material and changing the composition of the solid matter to iron powder 84 wt %, activated carbon 8 wt %, and pulp fiber 8 wt %. A heat-generating molded article was obtained in the same manner as in Example 1.

Example 9

A molded article was obtained in the same manner as in Example 1, except for using the pulp fiber of Example 2 but no flocculant. A heat-generating molded article was obtained in the same manner as in Example 1.

Example 10

A molded article was obtained in the same manner as in Example 1, except for using the pulp fiber of Example 2 and a carboxy ethyl cellulose salt having a degree of etherification of 0.65 and a 1% viscosity of 150 to 250 mPa·s (trade name: WS-C). A heat-generating molded article was obtained in the same manner as in Example 1.

Example 11

A molded article was obtained in the same manner as in Example 1, except for using the pulp fiber of Example 2 and changing the composition of the solid matter to iron powder 83 wt % activated carbon 8 wt %, and pulp fiber 9 wt %. The amount of charge of the slurry system during the preparation of the slurry composition was as follows.
Before flocculant addition: $-0.096 \times 10^{-7}$ (eq/g)
After cationic flocculant addition: $3.7 \times 10^{-7}$ (eq/g)
After anionic flocculant addition: $-0.028 \times 10^{-7}$ (eq/g)

Example 12

A molded article was obtained in the same manner as in Example 1, except for using the fibrous material and the solid matter composition of Example 11 and changing the amounts of the cationic and the anionic flocculants to 1.0 part by weight and 0.2 parts by weight, respectively. The amount of charge of the slurry system during the preparation of the slurry composition was as follows.
Before flocculant addition: $-0096 \times 10^{-7}$ (eq/g)
After cationic flocculant addition, $6.8 \times 10^{-7}$ (eq/g)
After anionic flocculant addition $1.2 \times 10^{-7}$ (eq/g)

Example 13

A molded article was obtained in the same manner as in Example 1, except for using the fibrous material and the solid matter composition of Example 11 and changing the amounts of the cationic and the anionic flocculants to 1.0 part by weight and 0.36 parts by weight, respectively. The amount of charge of the slurry system during the preparation of the slurry composition was as follows.
Before flocculant addition: $-0.096\times10^{-7}$ (eq/g)
After cationic flocculant addition: $6.8\times10^{-7}$ (eq/g)
After anionic flocculant addition $0.02\times10^{-7}$ (eq/g)

Example 14

A molded article was obtained in the same manner as in Example 1, except for using the fibrous material and the solid matter composition of Example 11 and changing the amounts of the cationic and the anionic flocculants to 2.0 part by weight and 0.72 parts by weight, respectively. The amount of charge of the slurry system during the preparation of the slurry composition was as follows.
Before flocculant addition: $-0.096\times10^{-7}$ (eq/g)
After cationic flocculant addition: $21\times10^{-7}$ (eq/g)
After anionic flocculant addition: $0.53\times10^{-7}$ (eq/g)

Example 15

A molded article was obtained in the same manner as in Example 1, except for using the fibrous material, the solid matter composition, and the flocculant system of Example 13 and reversing the order of addition of the flocculants. The amount of charge of the slurry system during the preparation of the slurry composition was as follows.
Before flocculant addition: $-0.096\times10^{-7}$ (eq/g)
After anionic flocculant addition: $-13\times10^{-7}$ (eq/g)
After cationic flocculant addition: $-0.087\times10^{-7}$ (eq/g)

Example 16

A molded article was obtained in the same manner as in Example 1, except that (1) the solid matter of the slurry system was 89 wt % of powder and 11 wt % of the fibrous material of Example 2, the powder being synthetic zeolite having carried thereon a copper/nickel/ruthenium ternary catalyst system for alcohol reaction and (2) the amounts of the cationic and the anionic flocculants were changed to 4.0 part by weight and 0.27 parts by weight, respectively, per 100 parts by weight of the solid matter. The amount of charge of the slurry system during the preparation of the slurry composition was as follows.
Before flocculant addition: $-0.62\times10^{-7}$ (eq/g)
After cationic flocculent addition: $4.4\times10^{-7}$ (eq/g)
After anionic flocculant addition: $0.16\times10^{-7}$ (eq/g)

Example 17

A molded article was obtained in the same manner as in Example 1, except that (1) the solid matter of the slurry system was 89 wt % of calcium carbonate powder (TP-123, available from Okutama Kogyo Co., Ltd.) and 11 wt % of the fibrous material of Example 2 and (2) the amounts of the cationic and the anionic flocculants were changed to 2.0 part by weight and 0.25 parts by weight, respectively, per 100 parts by weight of the solid matter. The amount of charge of the slurry system during the preparation of the slurry composition was as follows.
Before flocculant addition: $-0.072\times10^{-7}$ (eq/g)
After cationic flocculant addition: $5.1\times10^{-7}$ (eq/g)
After anionic flocculant addition: $0.87\times10^{-7}$ (eq/g)

Example 18

(1) Synthetic zeolite was put into a 1 liter flask. Copper nitrate, nickel nitrate, and ruthenium chloride dissolved in water were added thereto at a Cu:Ni:Ru molar ratio of 4:1:0.01 and the mixture was heated while stirring. At 90° C., a 10 wt % aqueous solution of sodium carbonate was slowly added dropwise to the mixture while controlling the pH within a range of 9 to 10. After one hour aging, the precipitate formed was collected by filtration, washed with water, dried at 80° C. for 10 hours and fired at 600° C. for 3 hours to obtain a catalytically active substance of powder form. The proportions of metal oxides and synthetic zeolite in the resulting catalytically active substance were 50 wt % and 50 wt %, respectively.

(2) Water was added to a blend of 10 parts by weight of pulp fiber (Mackenzie (trade name) from Fletcher Challenge Canada, Ltd.; CSF: 200 ml) and 90 parts by weight of the powdered catalytically active substance obtained in (1) above to give a solid concentration of 3 wt %. To the mixture were added 0.5 parts by weight of a cationic flocculant (polyamide-epichlorohydrin resin WS4020 (trade name) from Seiko PMC Corp.) and 0.25 parts by weight of an anionic flocculant (sodium carboxymethyl cellulose Cellogen WS-C (trade name) from Dai-ichi Kogyo Seiyaku Co, Ltd.) per 100 parts by weight of the solids content, followed by stirring well.

The mixture was diluted with water to a concentration of 0.5 wt % and converted into a wet web on a 250 mm by 250 mm square sheet machine (available horn Kumagai Riki Kogyo, Ltd.) in accordance with JIS P8209. The wet web was press-dried at 200° C. and 3 MPa to a water content of 1 wt % or less to obtain a catalyst film having a catalytically active substance supported therein. The amount of the catalytically active substance in the film was 65 wt %. The thickness of the film was 360 μm.

The resulting catalyst film was useful in the production of an aldehyde from a corresponding alcohol through a simple process in high yield.

Comparative Example 1

A molded article was obtained in the same manner as in Example 1, except for using pulp fiber having a CSF of 700 ml and a charge quantity of $-1.57\times10^{-6}$ eq/g and using no flocculants. A heat-generating molded article was obtained in the same manner as in Example 1.

Comparative Example 2

A molded article was obtained in the same manner as in Example 1, except for using pulp fiber of Example 4 having a CSF of 650 ml and a charge quantity of $-2.23\times10^{-6}$ eq/g and using no flocculants. A heat-generating molded article was obtained in the same manner as in Example 1.

Comparative Example 3

A molded article was obtained in the same manner as in Example 1, except for using the pulp fiber of Comparative Example 1 and changing the composition of the solid matter to iron powder 30 wt %, activated carbon 4 wt %, and pulp fiber 66 wt %. A heat-generating molded article was obtained in the same manner as in Example 1.

Comparative Example 4

A molded article was obtained in the same manner as in Example 1, except for using the fibrous material and the solid matter composition of Example 11 and adding only 1.0 part by weight of the cationic flocculant. The amount of charge of the slurry system during the preparation of the slurry composition was as follows.
Before flocculant addition: $-0.096 \times 10^{-7}$ eq/g)
After cationic flocculant addition: $6.8 \times 10^{-7}$ (eq/g)

Comparative Example 5

A molded article was obtained in the same manner as in Example 1, except for using the fibrous material and the solid matter composition of Example 11 and adding only 0.2 parts by weight of a polyacrylamide cationic flocculant (Accofloc C481, from Mitsui Cytec, Ltd.) as a flocculant system the amount of charge of the slurry system during the preparation of the slurry composition was as follows.
Before flocculant addition: $-0.096 \times 10^{-7}$ (eq/g)
After cationic flocculant addition: $4.7 \times 10^{-7}$ (eq/g)

Comparative Example 6

A molded article was obtained in the same manner as in Example 1, except for using the fibrous material and the solid matter composition of Example 11 and changing the amounts of the cationic and the anionic flocculants to 0.1 parts by weight and 0.1 parts by weight, respectively. The amount of charge of the slurry system during the preparation of the slurry composition was as follows.
Before flocculent addition: $-0.096 \times 10^{-7}$ (eq/g)
After cationic flocculant addition: $0.268 \times 10^{-7}$ (eq/g)
After anionic flocculant addition: $-2.4 \times 10^{-7}$ (eq/g)

Comparative Example 7

A molded article was obtained in the same manner as in Example 1, except for using the fibrous material and the solid matter composition of Example 11 and changing the amounts of the cationic and the anionic flocculants to 1.0 part by weight and 0.72 parts by weight, respectively. The amount of charge of the slurry system during the preparation of the slurry composition was as follows.
Before flocculant addition: $-0.096 \times 10^{-7}$ (eq/g)
After cationic flocculant addition: $0.268 \times 10^{-7}$ (eq/g)
After anionic flocculant addition: $-8.9 \times 10^{-7}$ (eq/g)

Measurement of Powder Content
The amount and composition of the powder in the resulting molded articles were measured with a thermogravimetric analyzer (TG/DTA 6200 from Seiko Instruments Inc.). In Examples 16 and 17, the powder composition was measured by ash content measurement in accordance with JIS P8128 (the sample was burnt at 525° C. for 2 hours).

Evaluation of Retention
The retention (%) was obtained by dividing the weight of the solid remaining on the papermaking wire by the weight of the solid matter fed to the wire part.

Evaluation by Tensile Strength
A 15 mm wide and 150 mm long specimen cut out of the molded article was subjected to a tensile test at an initial gauge length of 100 mm and a pulling speed of 20 mm/min in accordance with JIS P8113. A breaking length is calculated according to equation:

$$\text{Breaking length (m)} = (1/9.8) \times (\text{tensile strength (N/m)}) \times 10^6 / (\text{weight of test piece (g/m}^2))$$

Evaluation by Measurement of Heat Generation Characteristics
Two cut pieces of the molded article each measuring 80 mm by 100 mm and impregnated with the above-described electrolyte solution were stacked to provide a sample. The sample was put into a bag formed of an air-impermeable polyethylene sheet on one side and an air-permeable sheet (Breathron 1500 from Nitto Denko Corp.) on the opposite side. The open end of the bag was heat sealed to make a heat generating element. The temperature of the heat generating element was measured with a simplified temperature measuring device as specified in JIS S4100.

Evaluation of Formation
The molded article was held up to a light source and observed with the naked eye by the transmitted light. The formation was rated on the following A to C scale.
A: The transmitted light is uniform.
B: The transmitted light is non-uniform in part, but the quality of the molded article is acceptable.
C: The transmitted light is totally non-uniform, and the quality of the molded article is unacceptable.

Evaluation of Releasability of Wet Web From Papermaking Wire
After web formation, when the wet web was separated from the wire, the wire was inspected with the naked eye for any residue of the slurry composition remaining thereon. Releasability was rated on the following A to C scale based on the residue.
A: No residue
B: A slight residue is observed.
C: A considerable residue is observed.

TABLE 1

| | | Characteristics of Fibrous Material | | | | | |
| --- | --- | --- | --- | --- | --- | --- | --- |
| | | Frequency Distribution (%) | | Length-Weighted Average Length | CSF | Amount of Charge | |
| | Kind | Length: ≦0.4 mm | Length: 0.4-2.0 mm | (mm) | (cc) | ($10^{-6}$ eq/g) | Retention (%) |
| Example 1 | NBKP Mackenzie | 11.21 | 39.85 | 1.98 | 500 | −3.14 | 81.8 |
| Example 2 | NBKP Mackenzie | 12.55 | 42.75 | 1.86 | 150 | −3.66 | 85.7 |
| Example 3 | NBKP Mackenzie | 14.71 | 46.89 | 1.69 | 65 | −4.38 | 90.2 |

TABLE 1-continued

| | | Characteristics of Fibrous Material | | | | | |
|---|---|---|---|---|---|---|---|
| | | Frequency Distribution (%) | | Length-Weighted Average Length | CSF | Amount of Charge | |
| | Kind | Length: ≦0.4 mm | Length: 0.4-2.0 mm | (mm) | (cc) | ($10^{-6}$ eq/g) | Retention (%) |
| Example 4 | LBKP Cenibra | 15.05 | 84.73 | 0.7 | 300 | −6.51 | 90.4 |
| Example 5 | LBKP Cenibra | 21.18 | 78.39 | 0.63 | 130 | −7.29 | 93.3 |
| Example 6 | LBKP Cenibra | 27.08 | 72.78 | 0.58 | 50 | −9.94 | 93.1 |
| Example 7 | Mackenzie/ Cenibra = 50/50 | 19.94 | 70.03 | 0.9 | 140 | *1 | 87.4 |
| Example 8 | Mackenzie/ Cenibra = 50/50 | 21.99 | 60.61 | 1.07 | 55 | *2 | 87.1 |
| Example 9 | NBKP Mackenzie | 12.55 | 42.75 | 1.86 | 150 | −3.66 | 63.4 |
| Example 10 | NBKP Mackenzie | 12.55 | 42.75 | 1.86 | 150 | −3.66 | 76.2 |
| Compara. Example 1 | NBKP Mackenzie | 7.63 | 38 | 2.09 | 700 | −1.57 | 33.9 |
| Compara. Example 2 | LBKP Cenibra | 8.43 | 90.71 | 0.75 | 650 | −2.39 | 87.5 |
| Compara. Example 3 | NBKP Mackenzie | 7.63 | 38 | 2.09 | 750 | −1.57 | 90 |

*1: A blend of the pulp used in Example 2 and the pulp in Example 5
*2: A blend of the pulp used in Example 3 and the pulp in Example 6

TABLE 2

| | Characteristics of Molded Article | | | | | | | | | |
|---|---|---|---|---|---|---|---|---|---|---|
| | Composition (%) | | | Powder Content (%) | Thickness of Sheet (mm) | Basis Weight (g/m$^2$) | Tensile Characteristics | | Heat Generation Characteristics | |
| | | | | | | | Breaking Length (m) | Elongation (%) | Duration of Maintaining 38° C. or higher Temperature (min) | Maximum Temperature Reached (° C.) |
| | Iron Powder | Activated Carbon | Pulp | | | | | | | |
| Example 1 | 75.6 | 9.8 | 14.6 | 85 | 0.33 | 227 | 276 | 1.5 | 138 | 43.6 |
| Example 2 | 74.9 | 9.5 | 15.7 | 84 | 0.31 | 206 | 506 | 2.51 | 170 | 43.6 |
| Example 3 | 74.6 | 9.4 | 16.1 | 84 | 0.34 | 222 | 652 | 2.9 | 188 | 43.1 |
| Example 4 | 74.2 | 10.4 | 15.4 | 85 | 0.30 | 226 | 303 | 1.7 | 195 | 45 |
| Example 5 | 75.9 | 9.8 | 14.4 | 86 | 0.31 | 221 | 346 | 1.98 | 189 | 43.7 |
| Example 6 | 74.5 | 9.8 | 15.7 | 84 | 0.28 | 212 | 478 | 2.77 | 188 | 43 |
| Example 7 | 74.3 | 10 | 15.7 | 84 | 0.29 | 212 | 466 | 2.27 | 185 | 43.2 |
| Example 8 | 83.8 | 8.7 | 7.6 | 93 | 0.21 | 189 | 272 | 2.84 | 220 | 42.1 |
| Example 9 | 67.7 | 10.6 | 21.6 | 78 | 0.22 | 141 | 784 | 2.44 | 98 | 47.4 |
| Example 10 | 68.9 | 10.8 | 20.4 | 80 | 0.21 | 138 | 990 | 3.23 | 99 | 43.1 |
| Compara. Example 1 | 41.4 | 12.7 | 45.9 | 54 | 0.21 | 105 | 55 | 0.32 | 24 | 38.9 |
| Compara. Example 2 | 70.4 | 11.2 | 18.5 | 82 | 0.34 | 218 | 43 | 0.4 | 157 | 49.8 |
| Compara. Example 3 | 28.5 | 2.5 | 69 | 31 | 0.44 | 207 | 932 | 1.37 | 0 | 35.7 |

TABLE 3

| | | Flocculant Kind & Amount (part) | | Charge Quantity of Slurry System (eq) × $10^{-7}$ | | | | Solid Composition (%) | | | | | | | Flock Strength Reduction with time (%) |
|---|---|---|---|---|---|---|---|---|---|---|---|---|---|---|---|
| | | 1st Addn | 2nd Addn | Initial | After 1st Addn | After 2nd Addn | Charge Ratio | Retention (%) | Iron | Activated Carbon | Pulp | Weight (g/m²) | Formation | Sheet Releasability | |
| Example | 11 | WS4020 0.5 | HE1500F 0.18 | −0.096 | 3.7 | −0.028 | 38.5 | 86.6 | 9.4 | 81.4 | 9.2 | 202 | A | A | 38.4 |
| | 12 | WS4020 1.0 | HE1500F 0.2 | −0.096 | 6.8 | 1.2 | 70.8 | 84.3 | 6 | 79.8 | 11.2 | 205 | A | B | 39.0 |
| | 13 | WS4020 1.0 | HE1500F 0.36 | −0.096 | 6.8 | 0.02 | 70.8 | 92.6 | 8.3 | 81.7 | 10 | 223 | A | A | 39.9 |
| | 14 | WS4020 2.0 | HE1500F 0.72 | −0.096 | 21 | 0.53 | 218.8 | 95.2 | 9.5 | 80.4 | 10.2 | 231 | B | A | 53.1 |
| | 15 | HE1500F 0.36 | WS4020 1.0 | −0.096 | −13 | −0.087 | 135.4 | 87.8 | 9.3 | 80.6 | 10.1 | 211 | A | A | 40.4 |
| | 16 | WS4020 4.0 | HE1500F 0.27 | −0.615 | 4.4 | 0.18 | 7.2 | 99.9 | | *1 | | 240 | A | A | 32.3 |
| | 17 | WS4020 2.0 | HE1500F 0.25 | −0.072 | 5.1 | 0.869 | 70.8 | 86.7 | | *2 | | 208 | A | A | 50.0 |
| Comp. Example | 4 | WS4020 1.0 | none | −0.096 | 6.8 | — | 70.8 | 48.6 | 15.1 | 74.3 | 10.6 | 111 | A | C | *3 |
| | 5 | C481 0.2 | none | −0.096 | 4.7 | — | 49.0 | 74.6 | 10.7 | 78.2 | 11.1 | 181 | C | C | 88.3 |
| | 6 | WS4020 0.1 | HE1500F 0.1 | −0.096 | 0.268 | −2.4 | 2.8 | 58.6 | 11.5 | 78.2 | 10.4 | 147 | A | C | 78.2 |
| | 7 | WS4020 1.0 | HE1500F 0.72 | −0.096 | 6.8 | −8.9 | 70.8 | 85.9 | 9.5 | 79.9 | 10.6 | 206 | B | C | 81.1 |

*1: Solid composition of Example 16: catalyst/pulp = 82.7/17.3
*2: Solid composition of Example 17: calcium carbonate/pulp = 86.9/13.1
*3: Unmeasurable due to absence of peaks As is shown in Tables 1 and 2, the molded articles of Examples have high retention and excellent tensile and heat generation characteristics despite more than 50 wt % of the powder content. Those using the pulp fiber with stronger negative surface charge have higher retention and superior heat generation characteristics. Using short long fiber blended pulp brought about improvement in retention or sheet strength without changing the freeness and, in particular, achieves high retention even with a slurry composition having a high powder proportion making it possible to provide a molded article having a powder content as high as 93%. Moreover, the increased proportion of the oxidizable metal powder in the molded article makes it possible to for a thinner, more flexible sheet with greatly improved heat generation characteristics.

As is shown in Table 3, Examples 11 to 15 showed markedly improved results in retention, compositional ratio, formation, and wet sheet releasability from papermaking wire. In a papermaking test on an inclined short-wire paper machine, continuous sheet formation was possible to produce molded articles satisfying quality requirements. In Comparative Examples 4 to 7, in contrast, not all the requirements of retention, compositional ratio, formation, and wet sheet releasability from wire were satisfied. In a test on an inclined short-wire paper machine, stable continuous sheet formation was impossible because web breaks due to poor formation occurred, the slurry composition tended to remain on the wire, and web breaks ascribed to poor releasability from the wire occurred frequently.

It was also ascertained that the method of the present invention makes it feasible to produce a molded article having a high content of a catalytically active substance-containing powder (Examples 16 and 18) or a functional powder, such as calcium carbonate (Example 17) at high retention. The resulting molded articles were proved very uniform and superior in quality.

INDUSTRIAL APPLICABILITY

The present invention provides a molded article having a powder component fixed well on a fibrous material to achieve high retention and a method allowing for the production of such a molded article. The present invention provides a heat-generating molded article excellent in heat generation characteristics and strength.

The invention claimed is:

1. A molded article obtained by a wet papermaking process comprising:
   a powder that constitutes at least 50% by weight of the molded article, and
   a fibrous material
   that has a fiber length frequency distribution in which
   30% to 90% of the fibrous material has a fiber length of 0.4 to 2.0 mm and
   9% to 50% of the fibrous material has a fiber length of 0.4 mm or less.

2. The molded article according to claim 1, wherein the fibrous material has a Canadian standard freeness of 600 cc or less.

3. The molded article according to claim 1, wherein the fibrous material has an amount of charge of $-2.5 \times 10^{-6}$ eq/g or under.

4. The molded article according to claim 1, wherein the fibrous material has a length-weighted average fiber length of 0.3 to 2.0 mm.

5. A heat-generating molded article comprising the molded article according to claim 1 and an electrolyte solution impregnating the molded article.

6. The molded article of claim 1, wherein said fibrous material has a fiber length frequency distribution in which
40% to 80% of the fibrous material has a fiber length of 0.4 to 2.0 mm and
10% to 40% of the fibrous material has a fiber length of 0.4 mm or less.

7. The molded article of claim 1, wherein said fibrous material has a fiber length frequency distribution in which
45% to 75% of the fibrous material has a fiber length of 0.4 to 2.0 mm and
11% to 35% of the fibrous material has a fiber length of 0.4 mm or less.

* * * * *